US008293742B2

(12) United States Patent
Horn (10) Patent No.: US 8,293,742 B2
(45) Date of Patent: Oct. 23, 2012

(54) PREFERENTIAL VASOCONSTRICTION COMPOSITIONS AND METHODS OF USE

(75) Inventor: Gerald Horn, Deerfield, IL (US)

(73) Assignee: Alpha Synergy Development, Inc., Dana Point, CA (US)

( * ) Notice: Subject to any disclaimer, the term of this patent is extended or adjusted under 35 U.S.C. 154(b) by 385 days.

(21) Appl. No.: 12/460,941

(22) Filed: Jul. 27, 2009

(65) Prior Publication Data

US 2010/0029659 A1   Feb. 4, 2010

Related U.S. Application Data

(60) Provisional application No. 61/137,714, filed on Aug. 1, 2008, provisional application No. 61/192,777, filed on Sep. 22, 2008, provisional application No. 61/203,120, filed on Dec. 18, 2008, provisional application No. 61/207,481, filed on Feb. 12, 2009.

(51) Int. Cl.
*A61K 31/498* (2006.01)
*A61P 27/02* (2006.01)
(52) U.S. Cl. ..................................... 514/249
(58) Field of Classification Search .................. 514/249
See application file for complete search history.

(56) References Cited

U.S. PATENT DOCUMENTS

| | | | |
|---|---|---|---|
| 4,663,340 A | 5/1987 | Najer et al. | |
| 5,021,416 A | 6/1991 | Gluchowski | |
| 5,300,504 A | 4/1994 | Gluchowski | |
| 5,424,078 A | 6/1995 | Dziabo et al. | |
| 5,561,132 A | 10/1996 | Burke et al. | |
| 5,677,321 A | 10/1997 | Jeon et al. | |
| 5,756,503 A | 5/1998 | Burke et al. | |
| 5,804,587 A | 9/1998 | Cupps et al. | |
| 5,914,342 A | 6/1999 | Maurer et al. | |
| 5,916,900 A | 6/1999 | Cupps et al. | |
| 5,948,804 A | 9/1999 | Jeon et al. | |
| 5,965,595 A | 10/1999 | Maurer et al. | |
| 6,040,451 A | 3/2000 | Jeon et al. | |
| 6,087,361 A | 7/2000 | Munk et al. | |
| 6,110,952 A | 8/2000 | Henry et al. | |
| 6,117,871 A | 9/2000 | Maurer et al. | |
| 6,159,998 A | 12/2000 | Jeon et al. | |
| 6,162,818 A | 12/2000 | Henry et al. | |
| 6,242,442 B1 | 6/2001 | Dean et al. | |
| 6,534,048 B1 | 3/2003 | Borgman | |
| 6,562,873 B2 | 5/2003 | Olejnik et al. | |
| 6,627,210 B2 | 9/2003 | Olejnik et al. | |
| 6,641,834 B2 | 11/2003 | Olejnik et al. | |
| 6,673,337 B2 | 1/2004 | Olejnik et al. | |
| 6,730,065 B1 | 5/2004 | Horn | |
| 6,982,079 B2 | 1/2006 | Huth | |
| 7,019,149 B2 * | 3/2006 | Burk et al. ............ | 549/228 |
| 2005/0020600 A1 | 1/2005 | Scherer | |

OTHER PUBLICATIONS

Lee, "Efficacy of brimonidine tartrate 0.2% ophthalmic solution in reducing halos after laser in situ keratomileusis", J Cataract Refract Surg 2008, (34), pp. 963-967.*
Mechanism of decongestant activity of x2-adrenoceptor agnosits, Corboz M.R. et al., Pulmonary Pharmacology & Therapeutics 21 (2008) 449-454.

Alpha-adrenoceptor agonistic activity of oxymetazoline and xylometazoline, Haenisch B. et al., Fundam Clin Pharmacol. Dec. 17, 2009.
An Evaluation of Nasal Response Following Different Treatment Regimes of . . . , Morris S. et al., American Journal Rhinology, vol. 11, No. 2, Mar.-Apr. 1997, pp. 109-115(7).
Pharmacological Characterization of Postjunctional a-Adrenoceptors in . . . , Corboz M.R. et al., American Jour of Rhinology, vol. 19, No. 5, Sep.-Oct. 2005, pp. 495-502(8).
Postjuntional a2-adrenoceptors in blood ve3ssels of human nasal mucosa, Ichimura K. et al., Arch Otorhinolaryngol (1988) 245:127-131.
Long-term use of oxy- and xylometazoline nasal sprays induces rebound swelling, tolerance, and nasal hyperreactivity, Graf P., Rhinology 1996, 34(1):9-13.
Alpha 1-receptors at pre-capillary resistance vessels of the human nasal mucosa, Johannssen V et al., Rhinology 1997; 35(4):161-65.
Correspondence A Propos De L'article: <<Traitement Des Glaucomes Par La Brimonidine>>, M. Detry-Morel Et C. Dutrieux< J Fr Ophtalmo1.2001; 24(7): 748-9.
Potent a2A-Adrenoceptor-Mediated Vacoconstriction by Brimonidine in Porcine Ciliary Arteries, Anna Wikberg-Matsson, et al., IOVS, 2001, vol. 42, No. 9, 2049-55.
Medical Management of Chronic Rhinosinusitus—Jean P. Fong, MD, Matthew Ryan, MD (May 2006).
Preven Drugs from Going Missing in Action—Mark B. Abelson, MD, and Sarah A. Rosner MPH; Review of Ophthalmology; www.revophth.com/index.asp?page=1_357.htm.
Interactions Between CA2+ and H+ and Functional Consequences in Vascular Smooth Muscle—C. Austin and S. Wray, Journ. of Amer. Heart Association (Circ Res. 2000;86:355-363).
A Useful New Topical Treatment for Glaucoma and Ocular Hypertension—Drug Ther Perspect 13(1):1-4, 1999.
Brimonidine in the Treatment of Glaucoma and Ocular Hypertension—Louis B. Cantor, Therapeutics and Clinical Risk Management 2006:2(4) 337-346.
Silent Bedpartners—Nancy A. Collop, Chest 2002; 122; 1111-1112.
Traitement Des Glaucomes Par La Brimonidine (Alphagan® 0,2 %)—M. Detry-Morel, C. Dutrieux, J FR. Ophtalmol., 2000; 23, 8, 763-768.
Vasopressin-Induced Vasoconstriction: Two Concentration-Dependent Signaling Pathways—Kyle K. Henderson and Kenneth L. Bryon, J Appl Physiol 102: 1402-1409, 2007.
The Effect of Correction of Sleep-Disordered Breathing on Bp in Untreated Hypertension—K. Mae Hla, J. B. Skatrud, L. Finn, M. Palta and T. Young, Chest 2002;122; 1125-1135.

(Continued)

*Primary Examiner* — Sreeni Padmanabhan
*Assistant Examiner* — Sahar Javanmard
(74) *Attorney, Agent, or Firm* — Wood, Phillips, Katz, Clark & Mortimer (57) ABSTRACT

The invention generally relates to compositions and methods for preferential vasoconstriction of smaller blood vessels relative to larger blood vessels. The compositions comprise highly selective alpha-2 adrenergic receptor agonists, at low concentrations, such as below 0.05% weight by volume. The compositions preferably comprise brimonidine. The compositions preferably have pH between about 5.5 and about 6.5.

6 Claims, 7 Drawing Sheets

(5 of 7 Drawing Sheet(s) Filed in Color)

OTHER PUBLICATIONS

Myogenic Tone and Reactivity of the Rat Ophthalmic Artery—Y. P. R. Jarajapu, M. B. Grant, and H. J. Knot, Invest. Ophth. & Visual Science, Jan. 2004, vol. 45, No. 1.

Correspondence A Propos De L'article: <<Traitement Des Claucomes Par La Brimonidine>>, M. Detry-Morel Et C. Dutrieux, J Fr Ophtalmol. 2000; 23(8): 763-8.

Prospective Study of the Association Between Sleep-Disordered Breathing and Hypertension—P. Peppard, et. al., The New England J of Med., vol. 342, No. 19:1378-1384 (2000).

Catecholamines and Sympathomimetic Drugs—Goodman & Gilman's Pharmacology, Ch. 10; www.accessmedicine.com/popup.aspx?aID-936314&pring=yes_chapter.

Rhinitis Medicamentosa—JT Ramey, E Bailen, RF Lockey, J Investig Allergol Clin Immunol 2006; vol. 16(3); 148-155.

Characterization of three inhibitors of endothelial nitric oxide synthase in vitro and in vivo—D.D. Rees, et al., br. J. Pharmacol. (1990) 101, 746-752.

Inhibition of $\alpha$-adrenergic vasoconstriction in exercising human thigh muscles—D. Walter Wray, et al., J Physiol 555, 2 pp. 545-264 (2003).

Dexmedetomidine Enhances the Local Anesthetic Action of Lidocaine via . . . Tatsushi Yoshitomi DDS et al., Anesth Analg 2008; 107:96-101.

Adding Dexmedetomidine to Lidocaine for Intravenous Regional Anesthesia, Dilek Memis, MD et al., Anesth Analg 2004;98:835-40.

\* cited by examiner

Fig 4a: pretreatment baseline – contact lens irritation and allergic reaction

FIG. 4A

Fig 4b: Tetrahydrozoline 0.05% OD          Brimonidine 0.01% OS

Fig 4c: Oxymetazoline 0.025% OD          Brimonidine 0.02% OS

FIG. 4C

Fig 4d: Naphazoline 0.033% OD          Brimonidine 0.02% OS

FIG. 4D

Fig 4e: Brimonidine 0.033% OS only; 4 hours after 4d (effect lasted ~ 4 hours)

Vs. Baseline 11 hours earlier:

FIG. 4E

Baseline:

FIG. 5A

Right eye VISINE Original®  Left eye Brimonidine 0.012% x1 ii gtts tid, day 2 1st instillation  FIG. 5B  ii gtts tid, day 2 1st instillation Note rebound hyperemia Right eye Brimonidine 0.12% x1  Left eye Brimonidine 0.012%x1 ii gtts  FIG. 5C  ii gtts

FIG. 6

PREFERENTIAL VASOCONSTRICTION COMPOSITIONS AND METHODS OF USE

BACKGROUND OF THE INVENTION

Dilation of small blood vessels, particularly arterioles, capillaries, and venules, causes many clinically undesirable events including surface hemorrhage and hyperemia following Lasik surgery, eye redness (conjunctival hyperemia), and nasal congestion (turbinate mucosal swelling secondary to vasodilation).

Adrenergic receptors mediate physiological responses to the catecholamines, norephinephrine and epinephrine, and are members of the superfamily of G protein-coupled receptors having seven transmembrane domains. These receptors, which are divided pharmacologically into a-1, a-2 and β-adrenergic receptor types, are involved in diverse physiological functions including functions of the cardiovascular and central nervous systems. The a-adrenergic receptors mediate excitatory and inhibitory functions: a-1 adrenergic receptors are typically excitatory post-synaptic receptors which generally mediate responses in an effector organ, while a-2 adrenergic receptors are located postsynaptically as well as presynaptically, where they inhibit release of neurotransmitters. Agonists of a-2 adrenergic receptors currently are used clinically in the treatment of hypertension, glaucoma, spasticity, and attention-deficit disorder, in the suppression of opiate withdrawal, as adjuncts to general anesthesia and in the treatment of cancer pain. Vascular constriction is known to be mediated by a-adrenergic receptors.

a-2 adrenergic receptors are presently classified into three subtypes based on their pharmacological and molecular characterization: a-2A/D (a-2A in human and a-2D in rat); a-2B; and a-2C (Bylund et al., Pharmacol. Rev. 46:121-136 (1994); and Hein and Kobilka, Neuropharmacol. 34:357-366 (1995)). The a-2A, a-2B, and a-2C subtypes appear to regulate arterial and/or venular contraction in some vascular beds, and the a-2A and a-2C subtypes mediate feedback inhibition of norepinephrine release from sympathetic nerve endings. The a-2A subtype also mediates many of the central effects of a-2 adrenergic agonists (Calzada and ArtiZano, Pharmacol. Res. 44: 195-208 (2001); Hein et al., Ann. NY Acad. Science 881:265-271 (1999); and Ruffolo (Ed.), a-Adrenoreceptors: Molecular Biology, Biochemistry and Pharmacology S. Karger Publisher's Inc. Farmington, Conn. (1991)). The a-2A subtype also mediates potent constriction of the porcine, but not human, ciliary artery.

Many compounds having selective a-2 agonist activity are known and include brimonidine (which has been used for lowering intraocular pressure in patients with open-angle glaucoma or ocular hypertension), guanfacine (which has been used to control high blood pressure), dexmetidomidine (which has been used as a sedative, analgesic, sympatholytic and anxiolytic), and methyl dopa (which has been used as a centrally-acting ad renergic anti hypertensive).

The patent or application file contains at least one drawing executed in color. Copies of this patent or patent application publication with color drawing(s) will be provided by the Office upon request and payment of the necessary fee.

The clinically available compounds belong to the general category of a adrenergic receptor agonists. It is a known property of all a adrenergic receptor agonists, including brimonidine, to cause vasoconstriction. However, known formulations of brimonidine and other known a-2 adrenergic receptor agonists are associated with a high incidence of rebound hyperemia, or other side effects, in clinical use. For example, after as few as three doses of applying known formulations of a adrenergic receptor agonists, patients may develop secondary rebound hyperemia or secondary vasodilation. Brimonidine (5-bromo-6-(2-imidazolidinylideneamino)quinoxaline L-tartrate), a known selective alpha 2 agonist is associated with significant rebound hyperemia (primary or delayed onset vasodilation) in its current concentration range for treating glaucoma of about 0.1% to 0.2%.

Commercially available general alpha agonists for topical mucosal decongestant use (ophthalmic and nasal applications) include tetrahydrozoline, naphazoline, oxymetazoline, xylometazoline, methoxamine and phenylephrine. These agonists have high alpha 1 receptor agonist activity and are known to cause rebound hyperemia and medicamentosa. Accordingly, their clinical use is usually restricted to several hours or a few days, at most. Many individuals with mucosal congestion or hyperemia from chronic conditions such as dry eye, contact lens wear, allergic conjunctivitis, allergic rhinitis, nonallergic rhinitis, acute or chronic sinusitis, nasal polyposis, rhinitis secondary to pregnancy, or rhinitis due to nasal septal deviation or obstruction and asthma, particularly, allergic asthma require longer term agonist use. To the best of the inventor's knowledge, there are currently no means to induce effective vasoconstriction without concomitant ischemia caused by an excessive reduction in blood flow and a cascade of inflammatory mediators, resulting in undesirable clinical sequelae of rebound hyperemia, and or medicamentosa, a potentially prolonged inflammatory state that can last for several weeks or months of rebound mucosal congestion.

Thus, there is a need for new methods and formulations that would provide safe and long term vasoconstriction with reduced or minimized side effects, such as rebound hyperemia.

SUMMARY OF THE PRESENT INVENTION

The present invention is generally related to compositions and methods. for inducing vasoconstriction. One of the key discoveries of the present invention lies in using low doses of highly selective a-2 adrenergic receptor agonists to achieve vasoconstriction with significantly reduced hyperemia.

There are a variety of applications and dosage forms that can be utilized to apply the findings of the invention. For example, some applications include methods and compositions for: treating nasal congestion; inducing vasoconstriction; inducing preferential vasoconstriction of smaller blood vessels relative to larger blood vessels; reducing capillary permeability in a pulmonary condition; reversing rebound hyperemia; reducing activation of a-1 adrenergic receptors; and treating and preventing an allergic response with reduced rebound hyperemia.

The invention also encompasses using the compositions and methods of this invention for prophylactic reasons, for example, for prophylaxis of conditions including, but not limited to, asthma, upper respiratory disease, acute pharyngitis, acute sinusitis, acute tracheobronchitis, influenza, lower respiratory disease, acute bronchitis, bronchiolitis, and community acquired pneumonia (CAP).

The invention also relates to a metered dose dispenser comprising the aqueous compositions of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

For purposes of the present invention, the terms below are defined as follows.

The term "low concentrations" refers to concentrations from between about 0.0001% to about 0.05%; more preferably, from about 0.001% to about 0.025%; even more preferably, from about 0.01% to about 0.025%; and even more preferably, from about 0.01% to about 0.02% weight by volume.

The term "administered locally" refers to administering the compositions of the present invention approximately at the site where they will come into contact with a-2 adrenergic receptors. This term specifically excludes oral administration, intravenous injection, or transdermal patches which are not applied approximately at the spatial location of the area which is desired to be treated by the compositions of the present invention.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, Alphagan™, and UK14304.

The term "treating" refers to reversing, alleviating, inhibiting, or slowing the progress of the disease, disorder, or condition to which such term applies, or one or more symptoms of such disease, disorder, or condition.

The term "preventing" refers to prophylactic use to reduce the likelihood of a disease, disorder, or condition to which such term applies, or one or more symptoms of such disease, disorder, or condition. It is not necessary to achieve a 100% likelihood of prevention; it is sufficient to achieve at least a partial effect of reducing the risk of acquiring such disease, disorder, or condition.

The term "swollen nasal turbinates condition" includes, but is not limited to, nasal decongestion.

Vasoconstriction with Reduced Hyperemia

One aspect of the present invention refers to a surprising and unexpected finding that using highly selective a-2 agonists at low concentrations allows reducing, minimizing, and/or eliminating rebound hyperemia while optimally providing clinically equal or more effective vasoconstriction. Rebound hyperemia refers to induced vasodilation (instead of intended vasoconstriction) occurring, often with a lag time, after an application or, more typically, repeated applications of vasoconstrictors and characterized by engorgement of blood vessels (such as those in the conjunctiva or nasal mucosa), increased capillary permeability and leakage, and, in some cases, inflammatory sequelae (medicamentosa), frequently due to the use of an alpha 1 constricting drug and particularly, chronic use of a vasoconstricting drug.

Many, if not all, references in the prior art associated rebound hyperemia with all alpha agonists and considered the complication of rebound hyperemia to be intrinsic to vasoconstriction, wherein blood flow is reduced, causing attendant ischemia with some inflammatory cascade, precipitating rebound hyperemia in many cases and often leading to medicamentosa.

Contrary to these teachings, it was surprisingly and unexpectedly found that selective alpha-2 (a-2) adrenergic receptor agonists (which are also interchangeably referred to as "a-2 agonists" throughout the application) with extremely high selectivity for a-2 adrenergic receptors at low concentrations, well below those previously contemplated, can induce effective vasoconstriction with low incidence of rebound hyperemia as compared to the prior art, and low incidence of allergic reaction, including allergic blepharitis and follicular conjunctivitis. Further, the incidence of ischemia is significantly reduced through the use of compositions and methods of the present invention.

While not wishing to be bound to any particular theory, the inventor believes that rebound hyperemia is primarily associated with a-1 agonist activity. Thus, unless the binding affinity of a-2 agonists for a-2 over a-1 adrenergic receptors is sufficiently high, not sufficiently highly selective a-2 agonists will cause an undesirable a-1 receptor stimulation with attendant rebound hyperemia. Accordingly, it is desired to minimize a-1 agonist activity by using highly selective a-2 agonists.

Accordingly, in one embodiment, the invention generally relates to a method of treating or preventing rebound hyperemia comprising administering to a patient in need thereof a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In another embodiment, the invention relates to a surprising finding that an aqueous composition comprising a selective a-2 adrenergic receptor agonist, or a pharmaceutically acceptable salt thereof, can be used for the prevention or treatment of a disease or a condition by administering said aqueous composition to a patient in need thereof, wherein the concentration of said agonist in said aqueous composition is substantially lower than the concentration of said agonist normally used in the treatment of glaucoma.

In another embodiment, the invention generally relates to a composition for inducing vasoconstriction comprising a selective a-2 adrenergic receptor agonist having a binding affinity of 100 fold or greater for a-2 over a-1 adrenergic receptors, or a pharmaceutically acceptable salt thereof, and wherein said selective a-2 adrenergic receptor agonist is present at a concentration below about 0.05% weight by volume.

In yet another embodiment, the invention generally relates to a composition for inducing vasoconstriction comprising a selective a-2 adrenergic receptor agonist having a binding affinity of 100 fold or greater for a-2b and/or a-2c receptors over a-1 adrenergic receptors, or a pharmaceutically acceptable salt thereof, and wherein said selective a-2 adrenergic receptor agonist is present at a concentration below about 0.05% weight by volume.

Figure 5A:
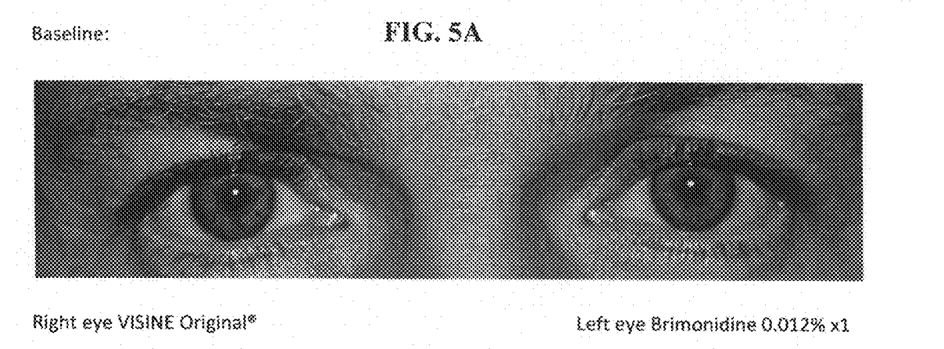
FIG. 5A is a baseline visual appearance of two eyes of a patient with an ocular condition of moderate hyperemia.
Figure 5B:
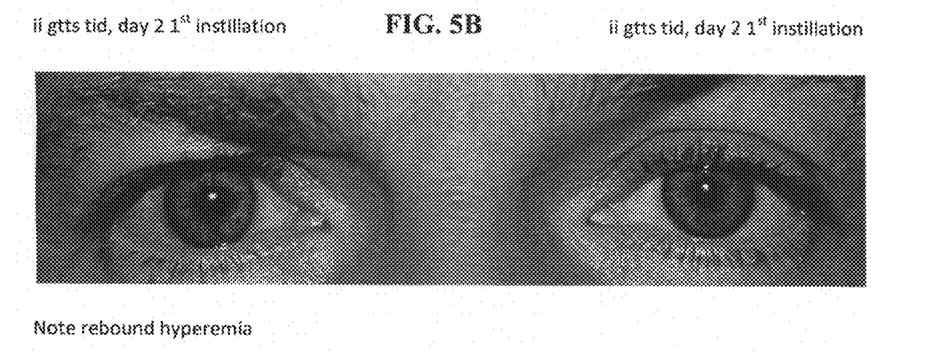
FIG. 5B depicts a visual appearance of the right eye of the patient after being treated with a prior art composition comprising VISINE Original® (tetrahydrozoline 0.05%) and the induction of rebound hyperemia, and the visual appearance of the left eye of the patient after being treated simultaneously with a composition of the present invention comprising brimonidine at 0.015%
Figure 5C:
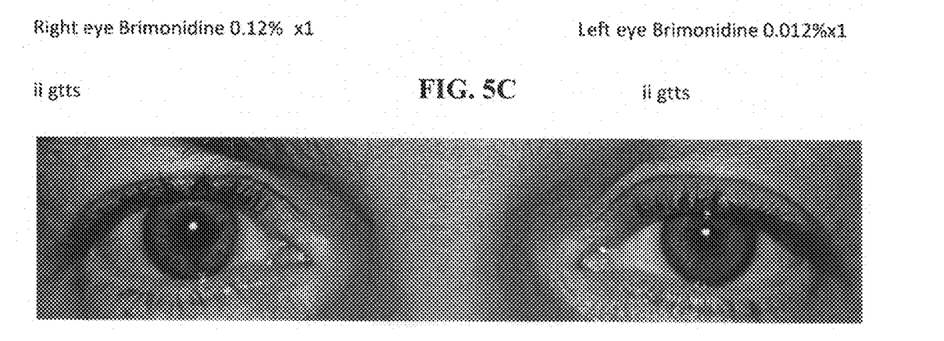
FIG. 5C depicts a visual appearance of the right eye of the patient after then being treated with the novel composition of the present invention comprising brimonidine at 0.015%, reversing the VISINE Original® induced rebound hyperemia, and a visual appearance of the left eye of the patient after being treated simultaneously with an additional drop of the composition of the present invention comprising brimonidine at 0.015%.

Further, it was surprisingly and unexpectedly found that selective a-2 adrenergic receptor agonists used at a concentration below about 0.05% weight by volume can reverse general/alpha 1 agonist induced hyperemia (instead of causing further ischemia from the induced vasoconstriction as would be expected for all agonists from prior art teachings), thereby providing a useful treatment for such patients and possibly alleviating medicamentosa from such drug applications, and possibly demonstrating a different mechanism of action for vasoconstriction than for alpha 1 agonists (FIGS. 5A-C).

In a preferred embodiment, the binding affinity of the selective a-2 adrenergic receptor agonist is about 500 fold or greater for a-2 over a-1 adrenergic receptors.

In a preferred embodiment, the selective a-2 adrenergic receptor agonist is present at a concentration between about 0.001% and about 0.025% weight by volume.

In a further preferred embodiment, the selective a-2 adrenergic receptor agonist is selected from the group consisting of apraclonidine, mivazerol, clonidine, brimonidine, alpha methyl dopa, guanfacine, dexemeditomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds.

In another preferred embodiment, the composition comprises brimonidine at a concentration between about 0.001% and about 0.025% weight by volume.

In a more preferred embodiment, a pH of the composition comprising the selective a-2 adrenergic receptor agonist is between about 5.5 and about 6.5.

In one embodiment, the invention generally relates to a composition for inducing vasoconstriction consisting essentially of brimonidine, wherein said brimonidine concentration is from between about 0.01% to about 0.02% weight by volume, wherein pH of said composition is between about 5.5 and about 6.5, and wherein said composition is formulated as an ocular drop.

In another embodiment, the invention generally relates to a composition for inducing vasoconstriction consisting essentially of brimonidine and potassium, wherein said brimonidine concentration is from between about 0.01% to about 0.02% weight by volume, wherein pH of said composition is between about 5.5 and about 6.5, and wherein said composition is formulated as an ocular drop.

In the most preferred embodiment, potassium is in the form of potassium chloride and its concentration is between about 0.2% to about 0.9% weight by volume.

Preferential Vasoconstriction

In one embodiment, methods of the present invention allow to induce preferential vasoconstriction of smaller blood vessels, such as capillaries and venules, relative to larger blood vessels, such as arteries and arterioles. These methods reduce activation of a-1 adrenergic receptors relative to a-2 adrenergic receptors.

Accordingly, in one embodiment, the invention generally relates to a method of effectively inducing preferential vasoconstriction of capillaries relative to arteries, and/or terminal arterioles, microvessels including capillary beds and/or venules with lower oxygen saturation than larger, proximal higher oxygen saturated arteries and or arterioles, comprising administering to a patient having an ocular or pulmonary condition, a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

By the term "effectively" it is understood that preferential vasoconstriction results in minimizing and/or eliminating ischemia.

While not wishing to be bound to any particular theory, this method allows constricting the blood flow to visible surface area with maximal constriction of microvasculature, together with minimal additional vasoconstriction of larger arterioles to maximize per unit area vasoconstrictive benefit and minimize ischemic consequence. This can be roughly analogized to reducing water flow at a sprinkler head rather than at the connection of the hose leading from the water supply to the sprinkler. Accordingly, this method allows achieving visibly effective whitening while optimizing total blood flow by minimizing arteriolar constriction to produce the best cosmetic and physiologic benefits of decongestant activity. Thus, the compositions and methods of the present invention make it possible to induce maximal microvessel constriction with the least arteriolar constriction.

The method can be used to treat various ocular and pulmonary conditions. In a preferred embodiment, a pulmonary condition may be associated with swollen nasal turbinates. In addition, preferential vasoconstriction of smaller blood vessels allows decreasing ischemia, inflammation, rhinitis medicamentosa, and rebound hyperemia.

The invention also relates to compositions formulated for inducing preferential vasoconstriction.

In one embodiment, a composition for inducing preferential vasoconstriction of smaller blood vessels relative to larger blood vessels comprises a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In another preferred embodiment, the method comprises administering to a patient having an ocular condition a composition comprising brimonidine, wherein said brimonidine concentration is between about 0.001% and about 0.025% weight by volume.

In a preferred embodiment, the invention generally relates to a method for inducing preferential vasoconstriction of smaller blood vessels relative to larger blood vessels comprising topically administering to a patient having an ocular condition a composition consisting essentially of brimonidine into ocular tissue, wherein pH of said composition is between about 5.5 and about 6.5, wherein said brimonidine concentration is from between about 0.001% to about 0.025% weight by volume and wherein said composition is formulated as an ocular drop.

Thus, in one embodiment, the invention generally relates to a composition for inducing preferential vasoconstriction consisting essentially of brimonidine into ocular tissue, wherein pH of said composition is between about 5.5 and about 6.5, wherein said brimonidine concentration is from between about 0.001% to about 0.025% weight by volume and wherein said composition is formulated as an ocular drop.

In one embodiment, the invention generally relates to administering compositions of the present invention within about 24 hours after a Lasik surgery on the patient.

In yet another embodiment, the invention generally relates to a method for inducing preferential vasoconstriction of smaller blood vessels relative to larger blood vessels comprising administering to a patient having an ocular or pulmonary condition a selective a-2 agonist having a binding affinity of 100 fold or greater for a-2b and or a-2c receptors over a-1 adrenergic receptors, or a pharmaceutically acceptable salt thereof, wherein said selective a-2 adrenergic receptor agonist is present at a concentration below about 0.05% weight by volume.

Reducing Capillary Permeability

In another embodiment, the invention generally relates to a method of reducing capillary permeability comprising administering locally to a patient in need thereof a selective a-2 adrenergic receptor agonist having a binding affinity of 100 fold or greater for a-2 over a-1 adrenergic receptors, or a pharmaceutically acceptable salt thereof, in the absence of a substantial amount of another therapeutic agent, wherein said selective a-2 adrenergic receptor agonist is present at a concentration below about 0.05% weight by volume.

In a preferred embodiment, the selective a-2 adrenergic receptor agonist is present at a concentration between about 0.001% and about 0.05% weight by volume.

The method can be used to treat various pulmonary conditions, including, but not limited to, bronchitis, including respiratory syncytial virus (RSV) bronchitis. In a preferred embodiment, a pulmonary condition may be associated with swollen nasal turbinates. In addition, reducing capillary permeability allows decreasing ischemia, inflammation, rhinitis medicamentosa, and rebound hyperemia.

The invention also relates to compositions for reducing capillary permeability. In one embodiment, the invention generally relates to a composition for reducing capillary permeability comprising administering to a patient in need thereof a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In one embodiment, the composition for reducing capillary permeability consists essentially of brimonidine, wherein pH of said composition is between about 5.0 and about 6.5, wherein said brimonidine concentration is from between about 0.001% to about 0.025% weight by volume, and wherein said composition is formulated as an aerosolized composition.

In another preferred embodiment, the method comprises administering to a patient in need thereof a composition comprising brimonidine, wherein said brimonidine concentration is between about 0.001% and about 0.025% weight by volume. Reducing capillary permeability can be exploited to decrease mucosal swelling and inflammation, such as occurs in the bronchial mucosal lumen of the respiratory tract from a variety of conditions, including influenza, bacterial pathogens, asthma, allergic asthma, and other causes of mucosal edema of the respiratory tract.

Reducing capillary permeability can also be exploited to decrease spread of viral and bacterial pathogens, thus potentially reducing the duration and morbidity of various infections, including but not limited to, infections caused by the flu virus.

In addition, reducing capillary permeability allows reducing, alleviating or decreasing ischemia, inflammation, rhinitis medicamentosa, and rebound hyperemia.

Also, reducing capillary permeability allows reducing and/or alleviating allergic or inflammatory conditions of the respiratory tract associated with a pulmonary condition, for example reducing the bronchiole mucosal edema and congestion.

In one embodiment, the invention generally relates to a method of reducing capillary permeability in a pulmonary condition associated with swollen nasal turbinates comprising administering to a patient in need thereof a composition consisting essentially of brimonidine, wherein pH of said composition is between about 3.5 and about 6.5, wherein said brimonidine concentration is from between about 0.001% to about 0.025% weight by volume, and wherein said composition is formulated as an aerosolized composition, and wherein the composition is administered into a nasal airway of the patient.

In a preferred embodiment, the invention generally relates to a method of reducing capillary permeability in a pulmonary condition associated with swollen nasal turbinates comprising administering to a patient in need thereof a composition consisting essentially of brimonidine, wherein pH of said composition is between about 5.0 and about 6.5, wherein said brimonidine concentration is from between about 0.001% to about 0.025% weight by volume, and wherein said composition is formulated as an aerosolized composition and administered into a nasal airway of the patient.

In another embodiment, the invention generally relates to a method of treating respiratory syncytial virus (RSV) bronchitis comprising administering to a patient in need thereof a composition consisting essentially of brimonidine, wherein pH of said composition is between about 5.0 and about 6.5, wherein said brimonidine concentration is from between about 0.001% to about 0.07%, more preferably, from between about 0.001% to about 0.03% weight by volume.

In another embodiment, compositions suitable for the methods of the present invention can be administered thorough oral ingestion in about the same concentration ranges that are suitable for the topical application.

Reversing Rebound Hyperemia

In one embodiment, the invention generally relates to a method of reversing rebound hyperemia comprising administering to a patient currently or previously undergoing administration of an a-1 adrenergic receptor agonist a selective a-2 adrenergic receptor agonist having a binding affinity of 100 fold or greater for a-2 over a-1 adrenergic receptors, or a pharmaceutically acceptable salt thereof, wherein said first selective a-2 adrenergic receptor agonist is present at a concentration below about 0.05% weight by volume.

By the term "previously undergoing" it is meant the administration (e.g. treatment with) of a-1 agonists that was sufficiently recent to cause rebound hyperemia in said patient.

In a preferred embodiment, the selective a-2 adrenergic receptor agonist is present at a concentration from between about 0.001% to about 0.035% weight by volume.

In another preferred embodiment, the method of reversing rebound hyperemia further decreases ischemia, inflammation, and rebound hyperemia associated with a-1 agonist use.

In another preferred embodiment, the invention generally relates to a composition for reversing rebound hyperemia comprising brimonidine, wherein said brimonidine concentration is between about 0.001% and about 0.025% weight by volume.

In a preferred embodiment, the composition further comprises a buffer, and wherein pH of said composition is between about 5.5 and about 6.5.

In another preferred embodiment, the composition for reversing rebound hyperemia consists essentially of brimonidine, wherein said brimonidine concentration is from between about 0.001% to about 0.025% weight by volume, wherein pH of said composition is between about 5.5 and about 6.5, and wherein said composition is formulated as an ocular drop.

In yet another preferred embodiment, the invention generally relates to a composition for reversing rebound hyperemia consisting essentially of brimonidine and a second adrenergic receptor agonist, wherein said brimonidine concentration is from between about 0.001% to about 0.025% weight by volume, wherein pH of said composition is between about 5.5 and about 6.5, and wherein said composition is formulated as an ocular drop.

Reducing Activation of a-1 Receptors

In another embodiment, the invention generally relates to a method of reducing activation of a-1 adrenergic receptors comprising administering to a patient having an ocular or pulmonary condition a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In a preferred embodiment, the selective a-2 adrenergic receptor agonist is present at a concentration between about 0.001% to about 0.025% weight by volume.

The method can be used to treat various ocular and pulmonary conditions. In a preferred embodiment, a pulmonary condition may be associated with swollen nasal turbinates (e.g., nasal decongestion). In addition, preferential vasoconstriction of smaller blood vessels allows decreasing ischemia, inflammation, rhinitis medicamentosa, and rebound hyperemia.

In another preferred embodiment, the method comprises administering to a patient having an ocular condition a composition comprising brimonidine, wherein said brimonidine concentration is between about 0.001% and about 0.025% weight by volume.

The invention also encompasses compositions formulated for reducing activation of a-1 receptors.

In one embodiment, the composition consists essentially of brimonidine, wherein pH of said composition is between about 5.5 and about 6.5, wherein said brimonidine concentration is between about 0.001% and about 0.025% weight by volume and wherein said composition is formulated as an ocular drop.

In a preferred embodiment, the invention generally relates to a method of reducing activation of a-1 adrenergic receptors comprising topically administering to a patient having an ocular condition a composition consisting essentially of brimonidine into ocular tissue, wherein pH of said composition is between about 5.5 and about 6.5, wherein said brimonidine concentration is from between about 0.001% to about 0.025% weight by volume and wherein said composition is formulated as an ocular drop.

In one embodiment, the invention generally relates to administering compositions of the present invention within about 24 hours after a Lasik surgery on the patient.

In another embodiment, the invention generally relates to a method of reducing activation of a-1 adrenergic receptors comprising administering to a patient having a nasal congestion, an ocular or pulmonary condition a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume, whereby the reduced a-1 adrenergic receptor activation is below the $ED_{50}$ for a-1 induced vasoconstriction larger arteries and/or arterioles.

Selective a-2 Adrenergic Receptor Agonists

Selective a-2 agonists that may be used for the purposes of the present invention have extremely high selectivity for a-2 adrenergic receptors, defined by their binding affinities ($K_i$) for a-2 over a-1 receptors of more than 100:1, more preferably 500:1, even more preferably 700:1, even more preferably 1000:1 or greater, and most preferably, 1500:1 or greater.

It is well within a skill in the art to design an assay to determine a-2/a-1 functional selectivity. As non-limiting examples, potency, activity or $EC_{50}$ at an a-2A receptor can be determined by assaying for inhibition of adenylate cyclase activity. Furthermore, inhibition of adenylate cyclase activity can be assayed, without limitation, in PC12 cells stably expressing an a-2A receptor such as a human a-2A receptor. As further non-limiting examples, potency, activity or $EC_{50}$ at an a-1A receptor can be determined by assaying for intracellular calcium. Intracellular calcium can be assayed, without limitation, in HEK293 cells stably expressing an a-1A receptor, such as a bovine a-1A receptor.

To the best of the inventor's knowledge, and not desiring to be bound by any specific theory or mechanism, it is believed by the inventor that the particularly preferred adrenergic receptor agonists for the purposes of the present invention are highly selective for a-2B and/or a-2C receptors, as opposed to a-2A receptors.

In one embodiment, the selective a-2 adrenergic receptor agonist is a compound which has binding affinity of about 100 fold or greater for a-2 over a-1 adrenergic receptors. When a2/a1 is less than about 500 fold but more than about 100 fold, a concentration of the selective a-2 agonist is preferably from about 0.01% to about 0.07%; and is more preferably from about 0.02% to about 0.04%.

In a preferred embodiment, the selective a-2 adrenergic receptor agonist is a compound which has binding affinity of about 500 fold or greater for a-2 over a-1 adrenergic receptors. When a2/a1 is less than about 800 fold but more than about 500 fold, a concentration of the selective a-2 agonist is preferably from about 0.005% to about 0.05%; and is more preferably from about 0.01% to about 0.02%.

In a more preferred embodiment, the selective a-2 adrenergic receptor agonist is a compound which has binding affinity of about 700 fold or greater for a-2 over a-1 adrenergic receptors. When a2/a1 is less than about 1200 fold but more than about 800 fold, a concentration of the selective a-2 agonist is preferably from about 0.001% to about 0.025%; and is more preferably from about 0.005% to about 0.01%.

In a more preferred embodiment, the selective a-2 adrenergic receptor agonist is a compound which has binding affinity of about 1000 fold or greater for a-2 over a-1 adrenergic receptors. When a2/a1 is less than about 2000 fold but more than about 1200 fold, a concentration of the selective a-2 agonist is preferably from about 0.0005% to about 0.01%; and is more preferably from about 0.0025% to about 0.005%.

In a more preferred embodiment, the selective a-2 adrenergic receptor agonist is a compound which has binding affinity of about 1500 fold or greater for a-2 over a-1 adrenergic receptors. When a2/a1 is more than about 2000 fold, a concentration of the selective a-2 agonist is preferably from about 0.0002% to about 0.005%; and is more preferably from about 0.001% to about 0.003%.

The selective a-2 adrenergic receptor agonist may be present at a concentration from between about 0.0001% to about 0.05%; more preferably, from about 0.001% to about 0.025%; even more preferably, from about 0.01% to about 0.025%; and even more preferably, from about 0.01% to about 0.02% weight by volume.

It is preferred that a concentration of a selective a-2 adrenergic receptor agonist be below its vasoconstriction vs. concentration plateau. Typically, the optimal concentration is 10% to 90% above the minimal threshold of measurable vasoconstriction for a particular a-2 agonist, or below that of the plateau maximum concentration, and is preferably within the about 25% to about 75% range of either of these benchmarks. The term "plateau maximum concentration" means the concentration above which there is no or minimal further vasoconstriction effect. Other considerations in choosing a selective a-2 adrenergic receptor agonist are blood brain permeability and any possible side effects and other systemic reactions.

In one embodiment, the selective a-2 adrenergic receptor is selected from the group consisting of apraclonidine, mivazerol, clonidine, brimonidine, alpha methyl dopa, guanfacine, dexemeditomidine, (+)-(S)-4-[1-(2,3-dimethyl-phenyl)-ethyl]-1,3-dihydro-imidazole -2-thione, 1-[(imidazolidin-2-yl)imino]indazole, and mixtures of these compounds: Analogs of these compounds that function as highly selective a-2 agonists may also be used in compositions and methods of the present invention.

In a more preferred embodiment, the selective a-2 adrenergic receptor is brimonidine in the form of tartrate salt.

Methods of Treatment and Compositions Thereto

The surprising and unexpected discoveries of the present invention potentially have application in treating a nasal congestion and a variety of ocular and pulmonary conditions.

a) Swollen Nasal Turbinates (e.g., Nasal Congestion)

Thus, in one embodiment, the invention generally relates to a method of treating diseases associated with swollen nasal turbinates (e.g. nasal congestion), comprising administering locally to a patient in need thereof a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In a preferred embodiment, the condition associated with swollen nasal turbinates is selected from the group consisting of nasal congestion, allergic rhinitis, asthma, sleep disorders, and sleep apnea.

In one embodiment, the invention generally relates to compositions formulated for treating diseases associated with swollen nasal turbinates. Compositions particularly useful for these purposes preferably comprise brimonidine at concentrations of from 0.01% to about 0.04%, and more preferably, from 0.02% to about 0.035%.

b) Ocular Conditions

Ocular conditions include, but are not limited to, red eye, including chronic red eye; ocular vascular congestion after Lasik surgery; prophylactic intraoperative and postoperative reduction of hemorrhage and hyperemia after Lasik surgery; preoperative hemorrhage and hyperemia prophylaxis prior to Lasik surgery; prophylactic diabetic retinopathy; macular edema such as that associated with diabetes; conditions of retinal degeneration such as glaucoma, macular degeneration such as age-related macular degeneration (ARMD) and retinitis.pigmentosa; retinal dystrophies; elevated baseline hyperemia in glaucoma patients; inflammatory disorders of the retina; vascular occlusive conditions of the retina such as retinal vein occlusions or branch or central retinal artery occlusions; retinopathy of prematurity; retinopathy associated with blood disorders such as sickle cell anemia; elevated intraocular pressure; ocular itch; damage following retinal detachment; damage or insult due to vitrectomy, retinal or other surgery; and other retinal damage including therapeutic damage such as that resulting from laser treatment of the retina, for example, pan-retinal photocoagulation for diabetic retinopathy or photodynamic therapy of the retina. Ocular conditions that can be prevented or alleviated by administering the topical formulations of the present invention further include, without limitation, generic and acquired optic neuropathies such as optic neuropathies characterized primarily by loss of central vision, for example, Leber's hereditary optic neuropathy (LEON), autosomal dominant optic atrophy (Kjer disease) and other optic neuropathies such as those involving mitochondrial defects aberrant dynamin-related proteins or inappropriate apoptosis; and optic neuritis such as that associated with multiple sclerosis, retinal vein occlusions or photodynamic or laser therapy. See, for example, Carelli et al., Neurochem. Intl. 40:573-584 (2002); and Olichon et al., J. Biol. Chem. 278:7743-7746 (2003). The term "ocular condition" also encompasses aesthetic conditions, for example, excessive redness of an eye. The methods and compositions of the present invention can be used with other ocular procedures, particularly cataract surgery, retinal surgery, pterygiae removal, and motility surgery. At the concentration range employed to eliminate hyperemia, endothelial cell pump dysfunction, and the high level of allergic reactions of the glaucoma class of brimonidine concentrations, no intraocular pressure effects are noted. This is important because in cosmetic use, while retention of normal intraocular pressure is desired, lowering of intraocular pressure is not a necessary or desirable parameter to reduce in a normotensive population.

When the methods and compositions of the present invention are used in conjunction with Lasik surgery, the preferred a-2 agonist is brimonidine at a concentration of from about 0.015% to about 0.05%, and more preferably, from about 0.020% to about 0.025%. In a preferred embodiment, a selective a-2 agonist's concentration has to be such that intraocular pressure is not substantially reduced and endothelial cell pump is not substantially inhibited.

It is a further discovery of the present invention that the dose response curve for intraocular pressure reduction for brimonidine is significantly different than that for its vasoconstrictive effects, as well as endothelial cell pump inhibition. Despite brimonidine having the same hyperemic profile and high incidence of rebound hyperemia in clinical use as apraclonidine, when this class of more selective compounds is optimized to its vasoconstrictive dose response range, it is shown to have superior vasoconstrictive effect with less rebound (See, FIG. 3).

c) Pulmonary Conditions

Pulmonary conditions include, but are not limited to vascular congestion, mucosal swelling of bronchi and bronchioles, bronchitis, respiratory syncytial virus (RSV) bronchitis, etc. Other pulmonary uses include treatment of increases in capillary permeability that further shrink the available lumen size of an airway. Such increases in capillary permeability occur in allergic rhinitis, common cold; influenza; asthma, acute respiratory distress syndrome, and acute lung injury. Such conditions can cause alveolar capillary increased permeability and capillary changes along the mucosal surface that swell the mucosa into the lumen. An increase in capillary permeability is known as one of the main features by which these pathogens are disseminated inside a host organism through cascade of inflammatory byproducts and other specific means of induction.

In one embodiment, the invention generally relates to a method for treatment of a pulmonary condition comprising delivering compositions of the present invention as an aerosol having mass medium average diameter predominantly between 1 to 10μ, produced by an inhaler, jet or ultrasonic nebulizer.

d) Other Conditions

The methods and compositions of the present invention may also be used in other clinical indications for vasoconstriction, such as treating the subcutaneous epidermal swelling observed along and around the lower eyelids or the venous dilation of hemorrhoids. The present invention further provides compositions formulated to relieve the vascular engorgement associated with dilated vessels of hemorrhoid tissue with less morbidity than epinephrine or phenylephrine used with prior art. Compositions particularly useful for these purposes comprise brimonidine at concentrations of from 0.01% to 0.05%.

The present invention further provides compositions formulated to relieve the vascular engorgement associated with dilated vessels of pulmonary bronchi and bronchioles, via inhalant vehicle, to relieve more effectively than prior art, with less morbidity than epinephrine, norepinephrine, or pseudoephedrine, mucosal swelling and congestion associated with colds, flu, and other productive cough. Compositions particularly useful for these purposes comprise brimonidine at concentrations of from 0.001% to 0.040%.

In addition, the methods and compositions of the present invention may be used during endotracheal intubation.

In another embodiment, the invention relates to a method of treating sore throat, comprising administering locally to a patient in need thereof a selective a-2 adrenergic receptor agonist having a binding affinity of 100 fold or greater for a-2 over a-1 adrenergic receptors, or a pharmaceutically acceptable salt thereof, in the absence of a substantial amount of another therapeutic agent, wherein said selective a-2 adrenergic receptor agonist is present at a concentration below about 0.01% weight by volume.

In a preferred embodiment, the invention generally relates to a method of scleral whitening without significant rebound hyperemia, comprising administering to a patient in need thereof a topical composition comprising a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

This method allows achieving a more effective scleral whitening (i.e., whiter shades of scleral color) than possible with prior art compositions and methods, as a result of more effective vasoconstriction that creates sufficient constriction of the capillary bed within the sclera to induce an overall whitening not observed with prior art, allowing for an improved cosmetic appearance.

For the methods of scleral whitening, the preferred a-2 agonist is brimonidine at a concentration of from about 0.01% to about 0.05%, and more preferably, from about 0.015% to about 0.02%.

The methods and compositions of the present invention may also be used to treat noninfectious conjunctival hyperemia (caused, for example, by lack of sleep, consumption of alcohol, or other noninfectious causes).

In another embodiment, the invention generally relates to a method of reducing redness in an eye, comprising administering to a patient in need thereof a topical composition comprising a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In a preferred embodiment, the administering step of the topical composition may be done through the use of a hydrophilic contact lens, wherein the hydrophilic lens comprises a reservoir for retaining the topical compositions of the present invention.

For the method of reducing redness in an eye, the preferred a-2 agonist is brimonidine at a concentration of from about 0.005% to about 0.015%.

In yet another embodiment, the invention generally relates to a method for lightening tissue coloration comprising administering locally to a patient in need thereof a topical composition comprising a selective a-2 adrenergic receptor agonist having a binding affinity of 100 fold or greater for a-2 over a-1 adrenergic receptors, or a pharmaceutically acceptable salt thereof, wherein said selective a-2 adrenergic receptor agonist is present at a concentration below about 0.05% weight by volume.

In a preferred embodiment, methods of the present invention allow administration of the selective a-2 agonists for approximately at least a week; for approximately two weeks; for approximately three weeks; for approximately one month; for approximately two months; for approximately between two months and one year; for approximately one year; and for approximately longer than one year. It is to be understood that it is within a skill in the art to determine the most appropriate time period of administration.

The low toxicity and low incidence of hyperemia with the compositions of the present invention enables their relatively frequent and long term use. For example, clinical study of brimonidine 0.5% tid for one month and brimonidine 0.2% bid for one year equate to clinical use for vasoconstriction of sixty times per day and sixteen times per day respectively for brimonidine 0.025%, a typical concentration of a preferred embodiment of the present invention. In most cases, if desired, treatment can be repeated as often as every two hours, or commonly once every three to four hours.

In general, low concentrations of vasoconstrictive agents can be applied for prolonged periods of time (for example, for several hours) for much greater therapeutic index in reaching affected superficial vascular regions. The etiology of conditions that may benefit from vasoconstrictors is largely due to vascular abnormalities, inflammatory changes, or other vascular responses to chemical modulation by emotional changes (flushing). In addition, systemic absorption is typically considerably reduced compared to mucous membranes. Facial rosacea, and in particular, acne rosacea have distribution along either side of the nasal bridge, under the eyelids, and frequently includes the lower eyelids.

Thus, for many facial applications of emollients or creams, the compositions of the present invention offer improved safety and efficacy as compared to higher concentrations of the prior art.

However, in one embodiment, the application time of the compositions of the present invention lasts not more than about five minutes. In another embodiment, the application time of the compositions of the present invention is less than one minute.

Based on the use of such molecules at much higher doses for chronic treatment of glaucoma, the treatment for vasoconstriction can also be used to treat chronic conditions. For example, treatments can be repeated over a period of several months to a year, and most likely several years, as is currently common for glaucoma treatment with this class of molecules.

Due to its high safety profile regarding adverse systemic toxicity, the compositions of the present invention may be used every two hours, or more commonly, every three to four hours with low incidence of hyperemia. The concentrations should be optimized for their vasoconstrictive dose response curve, which may differ from other desired clinical effects.

Combination Treatments

In addition to using low doses of highly selective a-2 agonists by themselves, the invention also provides methods for using these highly selective a-2 agonists in several combinatorial applications, for example in combinations with a-1 antagonists and in combinations with antihistamines.

A. Combinations With a-1 Antagonists a-1 antagonists have been shown to have the property of reducing scotopic and mesopic pupil dilation. a-1 agonists of prior art, such as naphazoline, tetrahydrozoline, and oxymetazoline, have an undesirable property of causing papillary dilation with attendant reduction in quality of vision in a significant percentage of individuals. The highly selective a-2 agonists of the present invention at the claimed concentrations do not cause papillary dilations.

The compositions and methods of the present invention may combine highly selective a-2 agonists, as defined by the present invention, with a-1 antagonists and/or selective a-1 antagonists to minimize hyperemia and optimize the concentration which can be used for maximum reduction of sympathomimetic induced low light pupil enlargement. This has important consequence for improving night vision in people with large pupils and increased higher order aberrations, or higher order aberrations from other causes (such as refractive surgery).

Phentolamine is a preferred pharmaceutical agent for such use. When combined with the present invention, its use is further optimized. Preferably, when used in combination, the highly selective a-2 agonists of the present invention are employed in ratios varying from about 0.02% to about 0.05%. Most preferably, the a-1 antagonist is phentolamine myrsalate, and its concentration is from about 0.01% to about 0.1%.

B. Combinations With Antihistamines

In another embodiment, the invention generally relates to a composition formulated for treating and/or preventing an allergic response with reduced rebound hyperemia, comprising a selective a-2 adrenergic receptor agonist having a binding affinity of 100 fold or greater for a-2 over a-1 adrenergic receptors, or a pharmaceutically acceptable salt thereof, and a histamine antagonist, wherein said selective a-2 adrenergic receptor agonist is present at a concentration below about 0.025% weight by volume.

In another preferred embodiment, the invention generally relates to a method of treating and/or preventing an allergic response with reduced rebound hyperemia comprising administering to a patient in need thereof the composition comprising a selective a-2 adrenergic receptor agonist having a binding affinity of 100 fold or greater for a-2 over a-1 adrenergic receptors, or a pharmaceutically acceptable salt thereof, and a histamine antagonist, wherein said selective a-2 adrenergic receptor agonist is present at a concentration below about 0.025% weight by volume.

In a preferred embodiment, the a-2 agonist is brimonidine at a concentration of from about 0.001% to about 0.025% weight by volume; and the preferred histamine antagonist is selected from the group consisting of loratadine, desloratadine, cetirizine, fexofenadine, acrivastine, ebastine, norastemizole, levocetirizine, and mizolastine.

In a preferred embodiment, the composition for treating and/or preventing an allergic response with reduced rebound hyperemia is an aerosolized composition.

In a preferred embodiment, the invention generally relates to a composition consisting essentially of brimonidine and pheniramine maleate, wherein said brimonidine concentration is from between about 0.001% to about 0.025% weight by volume, wherein pH of said composition is between about 5.5 and about 6.5, and wherein said composition is formulated as an aerosolized composition.

In a preferred embodiment, the invention generally relates to a composition consisting essentially of brimonidine and a nonsedating antihistamine, wherein said brimonidine concentration is from between about 0.001% to about 0.025% weight by volume, wherein pH of said composition is between about 5.5 and about 6.5, and wherein said composition is formulated as an aerosolized composition.

Compositions (Formulations)

The compositions of the present invention are preferably formulated for a mammal, and more preferably, for a human.

In one embodiment, the compositions of the present invention are topical compositions. In one embodiment, the topical composition is formulated for treating and/or preventing an ocular condition.

The topical compositions include, but are not limited to, ocular drops, ocular ointments, gels and creams. They may also include additional non-therapeutic components, which include, but are not limited to, preservatives, delivery vehicles, tonicity adjustors, buffers, pH adjustors, antioxidants, and water.

The preservatives include, but are not limited to, benzalkonium chloride, chlorobutanol, thimerosal, phenylmercuric acetate, or phenylmercuric nitrate. Vehicles useful in a topical ophthalmic composition include, but are not limited to, polyvinyl alcohol, povidone, hydroxypropyl methyl cellulose, poloxamers, carboxymethyl cellulose, hydroxyethyl cellulose and purified water. Some of the preferred preservatives include Blink® (Abbott Medical Optics®; active ingredient: polyethylene glycol 400 0.25%) and perborate. It is also possible to use a physiological saline solution as a major vehicle.

A tonicity adjustor also can be included, if desired, in a topical composition of the invention. Such a tonicity adjustor can be, without limitation, a salt such as sodium chloride, potassium chloride, mannitol or glycerin, or another pharmaceutically or ophthalmically acceptable tonicity adjustor.

Various buffers and means for adjusting pH can be used to prepare topical compositions of the invention. Such buffers include, but are not limited to, acetate buffers, citrate buffers, phosphate buffers and borate buffers. It is understood that acids or bases can be used to adjust the pH of the composition as needed. Topically acceptable antioxidants useful in preparing a topical composition include, yet are not limited to, sodium metabisulfite, sodium thiosulfate, acetylcysteine, butylated hydroxyanisole and butylated hydroxytoluene.

To make the topical compositions of the present invention, one can simply dilute, using methods known in the art, more concentrated solutions of selective a-2 agonists. The precise method of carrying out the dilutions is not critical. Any commonly used diluents, including preservatives described above in the application, suitable for topical solutions can be used.

In one embodiment, the topical compositions of the present invention are ophthalmic compositions. An ophthalmic composition contains an ophthalmically acceptable carrier, which can be any carrier that has substantially no long term or permanent detrimental effect on the eye to which it is administered. Examples of ophthalmically acceptable carriers include, but are not limited to, water, including distilled or deionized water; saline; and other aqueous media.

In another preferred embodiment, said composition is an aerosolized composition. In one embodiment, the aerosolized composition is formulated for treating and/or preventing a pulmonary condition.

It is within a skill in the art to prepare aerosolized compositions of the present invention.

The aerosolized compositions of the present invention are generally delivered via an inhaler, jet nebulizer, or ultrasonic nebulizer which is able to produce aerosol particles with size of between about 1 and 10 μm.

In one embodiment, the selective a-2 agonist may be formulated in about 5 ml solution of a quarter normal saline having pH between 5.5 and 6.5, preferably between 5.5 and 6.0.

In a preferred embodiment, the aerosolized composition comprises about 0.02% brimonidine in about 5 ml solution, which further comprises about 0.225% sodium chloride, and wherein said composition has a pH between about 5.5 and 6.5, preferably between 5.5 and 6.0.

In a preferred embodiment, a pH of the compositions of the present invention is less than about 7.0, preferably, between about 5.5 and about 6.5, more preferably between 5.5 and 6.0.

In another preferred embodiment, the compositions of the present invention further include potassium (i.e., K+). The term "potassium" includes, but is not limited to, potassium salt. Preferably, potassium is potassium chloride.

In another preferred embodiment, the compositions of the present invention further include calcium (i.e., $Ca^{2+}$). The term "calcium" includes, but is not limited to, calcium salt. Preferably, calcium is calcium chloride.

In yet another preferred embodiment, the compositions of the present invention comprise nitrous oxide inhibitors. In a preferred embodiment, the nitrous oxide inhibitors are selected from the group consisting of L-NAME, L-NIL, L-NIO, and L-canavine, or combinations thereof. Preferably, concentration of the nitrous oxide inhibitors is between about 0.005% and about 0.5% weight by volume.

In another embodiment, the compositions of the present invention can be included in a pharmaceutically suitable vehicle suitable for oral ingestion. Suitable pharmaceutically acceptable carriers include solid fillers or diluents and sterile aqueous or organic solutions. The active compound will be present in such pharmaceutical compositions in the amounts sufficient to provide the desired dosage in the range as described above.

Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for nasal, enteral or parenteral applications. The active ingredients may be compounded, for example, with the usual non-toxic, pharmaceutically and physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used.

In one embodiment, the compositions of the present invention can be administered locally via an intraocular or periocular implant, which can be, without limitation, biodegradable or reservoir-based. As used herein, the term "implant" refers to any material that does not significantly migrate from the insertion site following implantation. An implant can be biodegradable, non-biodegradable, or composed of both biodegradable and non-biodegradable materials; a non-biodegradable implant can include, if desired, a refillable reservoir. Implants useful for preventing or alleviating an ocular condition include, for example, patches, particles, sheets, plaques, microcapsules and the like, and can be of any shape and size compatible with the selected site of insertion, which can be, without limitation, the posterior chamber, anterior chamber, suprachoroid or subconjunctiva of the eye. It is understood that a useful implant generally releases the implanted ophthalmic composition at a therapeutically effective dose to the eye of the subject over an extended period of time. A variety of ocular implants and extended release formulations suitable for ocular release are well known in the art, as described, for example, in U.S. Pat. Nos. 5,869,079 and 5,443,505.

The present invention is more fully demonstrated by reference to the accompanying drawings.

Figure 1:
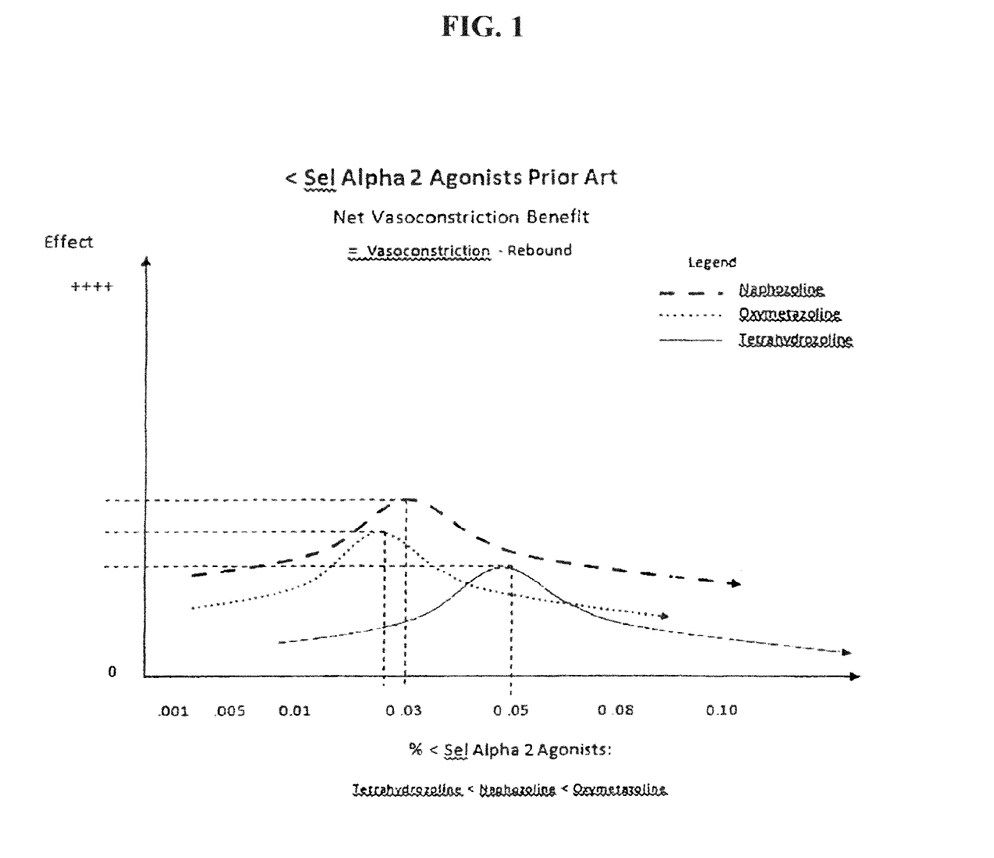
FIG. 1 is a graphical representation of the variation of vasoconstriction net clinical effectiveness of prior art compositions comprising naphazoline, oxymetazoline and tetrahydrozoline at various concentrations.

FIG. 1 depicts vasoconstrictive net clinical effectiveness for prior art a-agonists. Vasoconstrictive net clinical effectiveness is calculated by subtracting each compound's rebound hyperemic dose response curve from vasoconstrictive dose response curve. The general effectiveness and approximate optimal concentrations with the least rebound are revealed by the X-Y intersecting dashed lines. There is a slight peak for each molecule where its benefit to risk ratio is optimized. The reference concentration mark at 0.08% is to the right of the dose response data.

Figure 2:
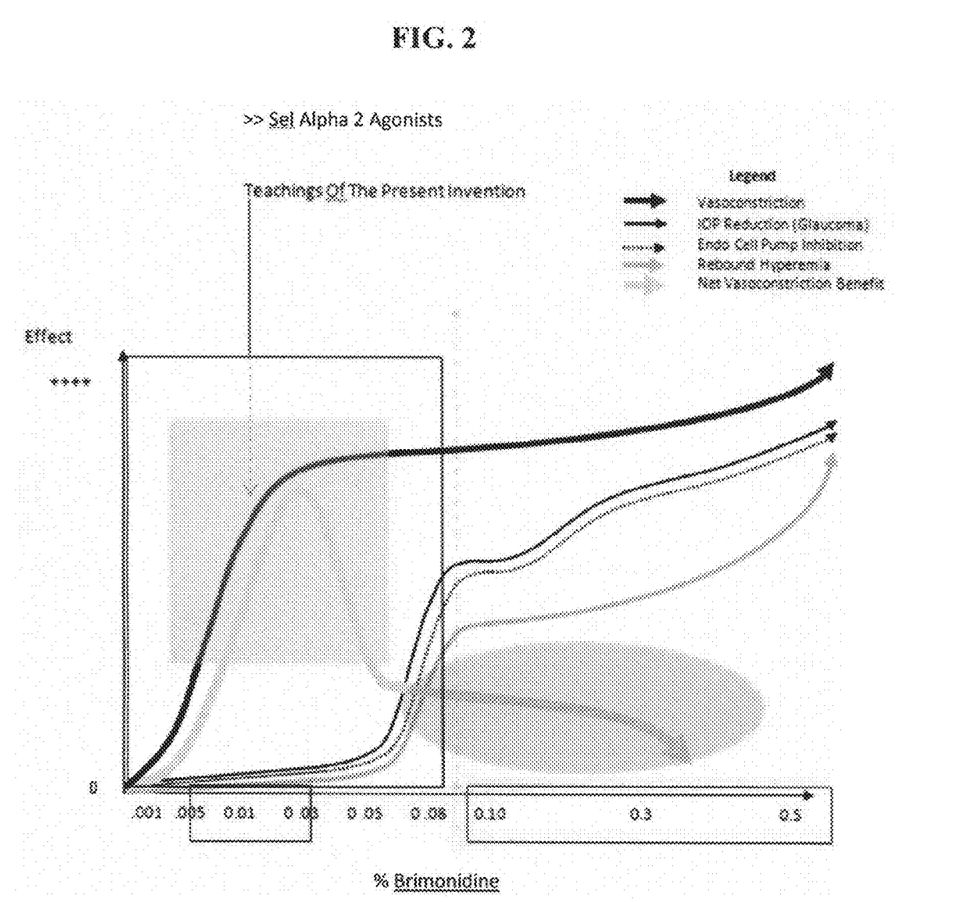
FIG. 2 is a graphical representation of the variation of vasoconstriction clinical effectiveness of compositions of the present invention comprising brimonidine at low concentrations.

FIG. 2 highlights the key discoveries of the present invention. It depicts a plot of vasoconstriction effect versus various concentrations of brimonidine, a selective a-2 agonist of the present invention. Vasoconstrictive effect when studied at reduced concentrations is shown to have been above its maximum dose response benefit, while intraocular pressure reduction and corneal endothelial cell pump inhibition are shown to have been just at their maximum at about 0.09%. As a result, there is an exponential drop-off in intraocular pressure reduction and endothelial cell pump inhibition just below 0.08%, while vasoconstrictive effect remains largely unchanged at these lower concentrations until much lower concentrations are reached.

It also demonstrates that concentrations of brimonidine of 0.10% and higher induce a large enough population of a-1 agonists to achieve rebound virtually identical to tetrahydrozaline, naphazoline and oxymetazoline; and may contribute an excessive number of a-2 receptors as well. FIG. 2 demonstrates that highly selective a-2 agonists defined by their binding affinities ($K_i$) for a-2 over a-1 receptors of more than 100:1, more preferably 500:1, even more preferably 700:1, even more preferably 1000:1 or greater, and most preferably, 1500:1 or greater, results in an optimized concentration range for optimal vasoconstriction without rebound hyperemia.

Figure 3:
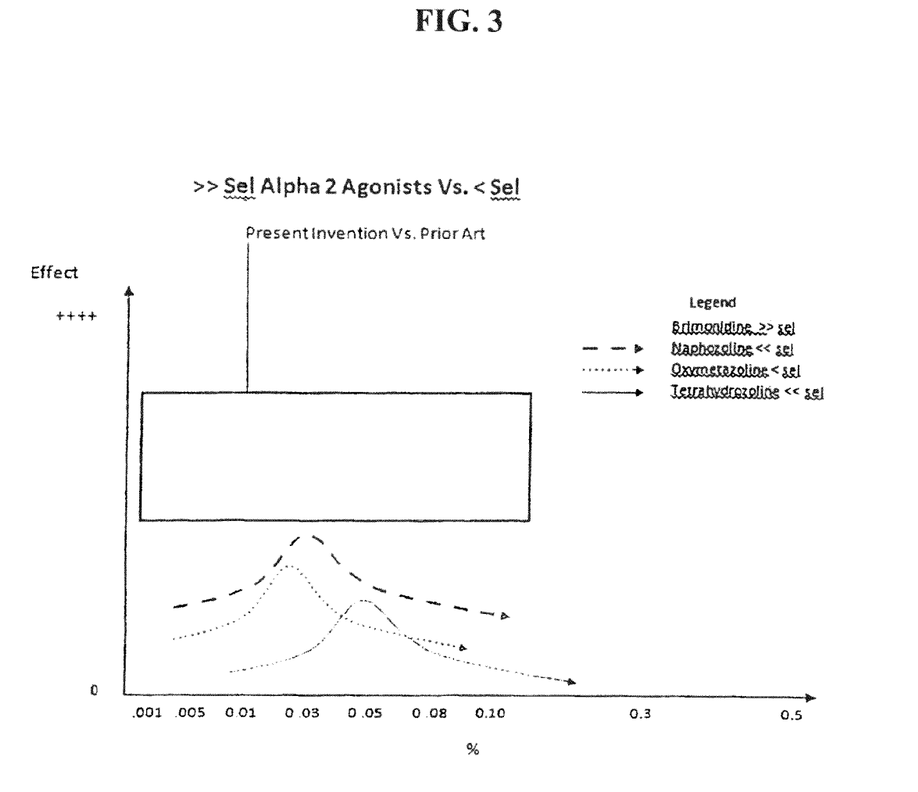
FIG. 3 is a graphical representation of clinical effectiveness of the compositions of the present invention versus prior art compositions.

FIG. 3 depicts a graphical representation of clinical effectiveness of the compositions of the present invention versus prior art compositions. The net effect of this improved vasoconstrictive benefit of a-2 predominant receptor activation and reduced rebound is highlighted for brimonidine in FIG. 3 relative to a-agonist vasoconstrictors in current clinical use. The potency and reduced morbidity allow for additional benefits of the subclass of more highly selective a-2 agonists as defined by the present invention.

FIG. 4 contains graphical representations of results of Example 1 and will be explained more fully in the section of the application dealing with Example 1.

FIGS. 5A-C demonstrate the unexpected discovery that novel and highly selective a-2 compositions of the present invention can reverse pre-induced rebound hyperemia of general alpha agonists.

FIG. 5A is a baseline visual appearance of two eyes of a patient with an ocular condition.

FIG. 5B depicts a visual appearance of the right eye of the patient after being treated with a prior art composition comprising VISINE Original® (Johnson & Johnson's registered trademark; active ingredient: tetrahydrozoline HCL 0.05%) and the induction of rebound hyperemia, and the visual appearance of the left eye of the patient after being treated simultaneously with a composition of the present invention comprising brimonidine at 0.015%.

FIG. 5C depicts a visual appearance of the right eye of the patient after then being treated with the novel composition of the present invention comprising brimonidine at 0.015%, reversing the VISINE Original® induced rebound hyperemia, and a visual appearance of the left eye of the patient after being treated simultaneously with an additional drop of the composition of the present invention comprising brimonidine at 0.015%.

Figure 6:
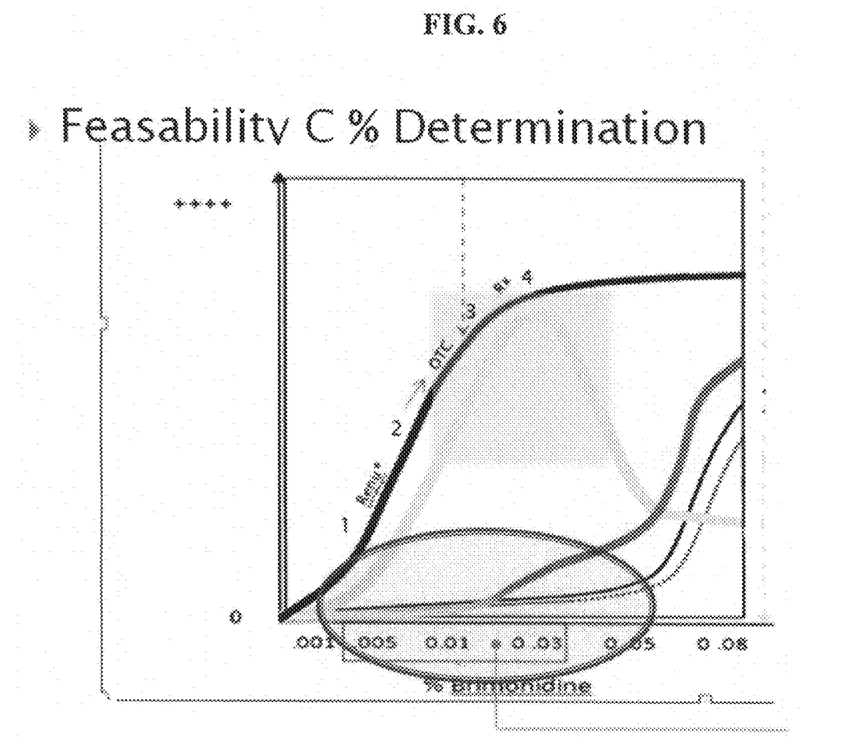
FIG. 6 is another graphical representation of clinical effectiveness of the compositions of the present invention versus prior art compositions.

FIG. 6 depicts a graphical representation of a finding of the present invention that an increased rebound hyperemia begins at around 0.03% for brimonidine. It thus demonstrates that the net effectiveness of brimonidine as a decongestant is greatest between about 0.01% and about 0.03%; preferably, between about 0.012% and about 0.02%

The following Examples are provided solely for illustrative purposes and are not meant to limit the invention in any way.

EXAMPLES

Example 1

In this Example, a patient was treated with brimonidine at claimed concentrations and prior art compositions of tetrahydrozoline, oxymetazoline and naphazoline.

The results clearly demonstrate significant scleral whitening brightening effects of treatment with brimonidine as compared with treatment with prior art compositions.

The results are shown in FIGS. 4A through 4E.

Figure 4A:
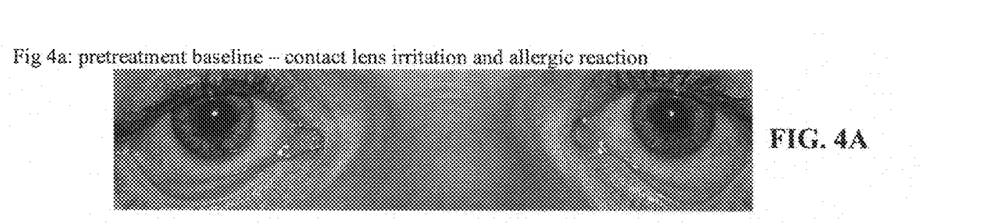
FIG. 4A is a baseline visual appearance of two eyes of a patient with an ocular condition.

FIG. 4A shows the base line for both eyes.

Figure 4B:
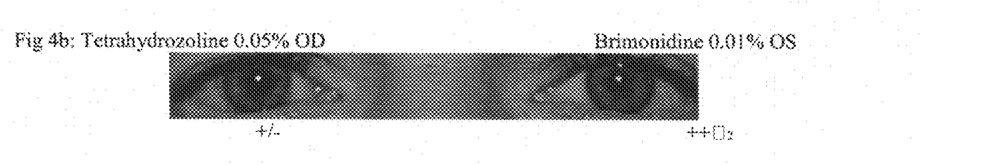
FIG. 4B depicts the eyes of the patient 180 minutes after being treated with a prior art composition comprising tetrahydrozoline at 0.05% (right eye) and a composition of the present invention comprising brimonidine at 0.01% (left eye).

FIG. 4B shows a comparison after 180 minutes, where the right eye has been treated with tetrahydrozoline at 0.05% and the left eye was treated with brimonidine at 0.01%

Figure 4C:
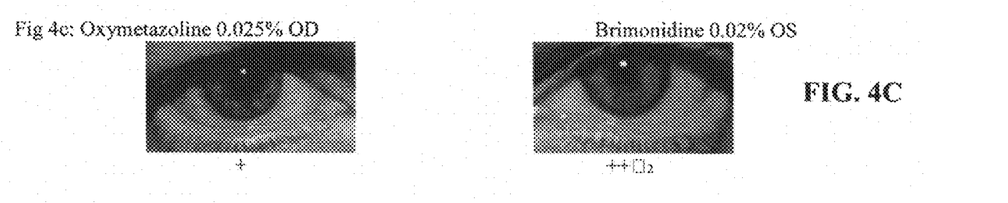
FIG. 4C depicts the eyes of the patient 240 minutes after baseline (FIG. 4A) after being treated with a prior art composition comprising oxymetazoline at 0.025% (right eye) and a composition of the present invention comprising brimonidine at 0.02% (left eye).

FIG. 4C shows a comparison four hours after baseline (FIG. 4A), where the right eye has been treated with oxymetazoline at 0.025% and the left eye was treated with brimonidine at 0.02%

Figure 4D:
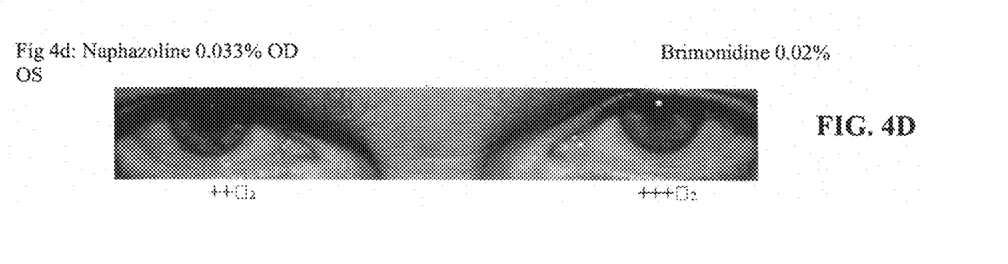
FIG. 4D depicts the eyes of the patient 240 minutes after treatment described in FIG. 4C after being treated with a prior art composition comprising naphazoline at 0.033% (right eye) and a composition of the present invention comprising brimonidine at 0.02% (left eye).

FIG. 4D shows a comparison where after a further four hours, the right eye has been treated with naphazoline at 0.033%; and the left eye was treated with brimonidine at 0.02%.

Figure 4E:
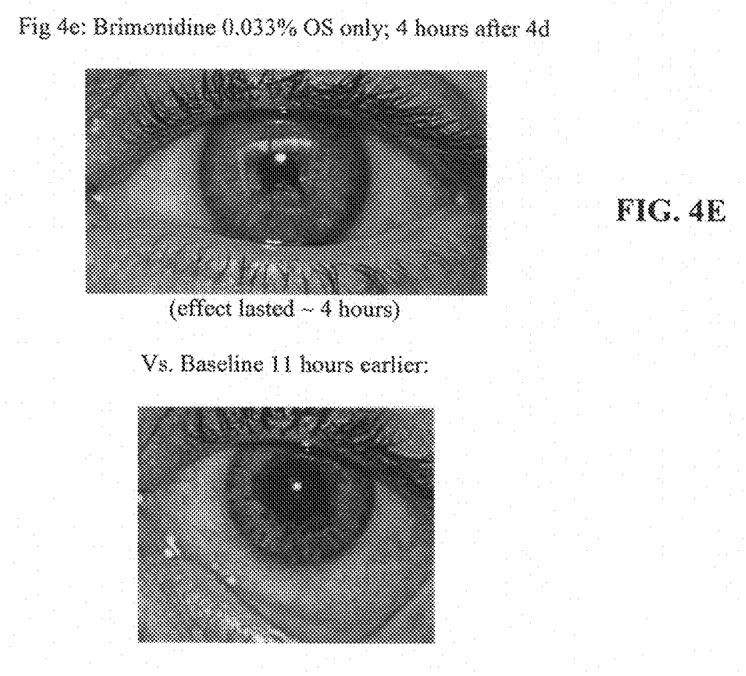
FIG. 4E depicts the left eye of the patient 240 minutes after treatment described in FIG. 4D after being treated with a composition of the present invention comprising brimonidine at 0.033%.

FIG. 4E shows the effect of brimonidine at 0.033% on the left eye only, 4 hrs after the effect shown in FIG. 4D (showing the third application to be without rebound hyperemia).

The effectiveness in most clinical situations is likely to be even greater, since baseline redness was at b 4/4 for this test. In an average clinical situation, baseline redness is at 1-1.5/4.

Accordingly, the results show that compositions of the present invention may be used every three to four hours with low incidence of hyperemia.

Example 2

Lasik Prophylaxis

Baseline:

Treatment of 200 patients via the Intralase femtosecond laser with no pretreatment for vasoconstriction—significant postoperative hyperemia and conjunctival hemorrhage with @15% petichial or larger hemorrhage when patients were seen postoperative day 1,25% 1+(14) hyperemia first hour+; 50% 2.5+hyperemia first how +; 25% 3+hyperemia first hour +. Flap dislocation rate: <0.1%.

Treatment group 1:

Naphcon-A® (Alcon, Inc; active ingredients: naphazoline hydrochloride 0.25% and pheniramine maleate 0.3%; preserved with benzalkoniurnm chloride) was used on a second group of 50 patients (85 procedures), 12% petichial or larger hemorrhage. 35% 1+hyperemia; 35% 2+hyperemia; 15% 2.5+hyperemia; 15% 3+hyperemia. Some clinical benefit noted. Flap dislocation rate: <0.1%.

Treatment group 2:

Brimonidine 0.2%, used off label, has been reported to cause flap dislocation rates of 5-10% and is currently not indicated nor recommended for this purpose.

Brimonidine 0.02% on 16 eyes, with no adverse effects or significant change in intraocular pressure, mean blood pressure or pulse noted.

Treatment Group 3:

Brimonidine 0.02% applied topically l-ii gtts per eye, 10-20 minutes preoperatively to an initial trial of 10 patients (100 eyes). <5% petichial or larger hemorrhage; 75% 1+hyperemia or less; 20% 2+hyperemia; 5% 2.5+hyperemia, flap dislocation rate just under 1%.

This group has been expanded to include over 500 eyes with similar results. A markedly different white quiet eye is noted in most patients, with no or only trace hyperemia found in the majority of the 1+ or less hyperemic group. Flap dislocation rate remains just under 1% with most of these mild striae as opposed to actual dislocation, similar to that found with Group 0 and 1.

Cosmetically, the patients are much improved from day 1 vs. no vasoconstrictor and vs. Naphcon-A. No adverse cardiovascular events occurred. No significant allergic reactions have been found.

Example 3

0.03% Brimonidine Nasal Spray: 0.9% saline vehicle used and nasal spray administered to patient with nasal congestion. This was repeated for one week without rebound. Complete relief for 3-5 hours was reached per application for treatment of moderate nasal congestion thought to be allergic in nature. Repeat applications×four hours without rebound. Patient population for this test limited to n of 1.

The proper dose response range can be tested with no more than routine experimentation.

Example 4

Eighteen patients having a red eye condition were treated with a composition of the present invention (i.e., brimonidine at 0.018%) and with VISINE Original®. Three patients withdrew from the study prior to completion.

The patients were assigned "cumulative red scores", prior to each administration (as baseline) and then 10 min after each dose, by dividing the bulbar conjunctiva into six sectors, each scored with a grade 1-3 score and the total cumulative score. In terms of initial efficacy of the active vs. VISINE Original® the patients were calculated to have 68.71% reduction in redness score after administration of a single dose of brimonidine at 0.018%, and 31.06% reduction in redness score after administration of VISINE Original® after a single application.

Rebound hyperemia after one dose occurred only in 6.6% after administration of brimonidine at 0.05% (1 of 15) and in 26.6% after administration of VISINE Original®.

The three week scores also demonstrated advantages of the compositions of the present invention: after administration of brimonidine at 0.018%, the average redness count went down from 10.3 to 1.6; after administration of VISINE Original®, the average redness count went down from 8.8 to 2.5. However, it is possible that due to the length of the study and inadvertent dilution of preservative in formulation, contamination of the brimonidine 0.018% composition may have occurred towards the end.

Example 5

Seven patients with chronic red eyes were treated as follows: one eye was treated with extreme low dose (eld) brimonidine at 0.015% and the other eye was treated with Naphcon-A®. The treatment was through drops twice a day for three to five weeks. At the end, patient satisfaction assessment was conducted.

All patients reported reduced redness on eld brimonidine.

42% preferred eld brimonidine.

0% preferred Naphcon-A®.

The invention claimed is:

1. A method for reducing eye redness consisting essentially of administering brimonidine to a patient having an ocular condition, wherein brimonidine is present at a concentration between about 0.001% weight by volume and about 0.05% weight by volume.

2. The method of claim 1, wherein brimonidine is present at a concentration between about 0.001% to about 0.025% weight by volume.

3. A method for reducing eye redness consisting essentially of topically administering to a patient having an ocular condition a composition consisting essentially of brimonidine into ocular tissue, wherein pH of said composition is between about 5.5 and about 6.5, wherein said brimonidine concentration is between about 0.001% and about 0.025% weight by volume and wherein said composition is formulated as an ocular drop.

4. The method of claim 3, wherein said composition is topically administered within about 24 hours after a Lasik surgery on said patient.

5. The method according to claim 1, wherein said ocular condition is chronic red eye.

6. The method according to claim 3, wherein said ocular condition is chronic red eye.

* * * * *